US007681573B2

(12) United States Patent
Matthiessen et al.

(10) Patent No.: US 7,681,573 B2
(45) Date of Patent: Mar. 23, 2010

(54) COMPRESSED AIR RESPIRATOR

(75) Inventors: Hans Matthiessen, Bad Schwartau (DE); Kai Kück, Hamburg (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 945 days.

(21) Appl. No.: 11/372,178

(22) Filed: Mar. 9, 2006

(65) Prior Publication Data

US 2006/0260610 A1 Nov. 23, 2006

(30) Foreign Application Priority Data

May 20, 2005 (DE) ....................... 10 2005 023 392

(51) Int. Cl.
*A61M 16/00* (2006.01)
*A62B 7/00* (2006.01)

(52) U.S. Cl. ............................ 128/204.18; 128/200.24; 128/203.18; 128/201.25; 128/203.25; 128/205.12

(58) Field of Classification Search ............ 128/204.18, 128/201.13, 203.18, 201.25, 200.24, 203.25, 128/205.12
See application file for complete search history.

(56) References Cited

U.S. PATENT DOCUMENTS

| | | | | |
|---|---|---|---|---|
| 3,913,576 A | | 10/1975 | Martin et al. | |
| 4,031,887 A | * | 6/1977 | Botos et al. | 128/205.12 |
| 4,423,723 A | * | 1/1984 | Winkler et al. | 128/202.22 |
| 4,428,372 A | * | 1/1984 | Beysel et al. | 128/202.26 |
| 4,793,340 A | * | 12/1988 | Ottestad | 128/200.24 |
| 5,810,002 A | * | 9/1998 | Dittmann | 128/203.12 |

(Continued)

FOREIGN PATENT DOCUMENTS

| | | |
|---|---|---|
| GB | 855 728 | 12/1960 |

(Continued)

*Primary Examiner*—Justine R Yu
*Assistant Examiner*—Colin Stuart
(74) *Attorney, Agent, or Firm*—McGlew and Tuttle, P.C.

(57) ABSTRACT

A compressed air respirator with prolonged operating time due to rebreathing. The compressed air reservoir includes a compressed air reserve with a connected demand air supply valve, a reversible breathing gas reservoir (4) with a registering device (5) detecting the filling level of the breathing gas reservoir (4), and with an inspiration and expiration line (7, 8) for the user of the apparatus. A valve (6) is connected with the inspiration and expiration line (7, 8) and, on the inlet side, with the compressed air reserve (1) with a demand air supply valve (2) and with the breathing gas reservoir (4) and, on the outlet side, with the ambient air (11) and with the breathing gas reservoir (4). The valve means (6) is cyclically reversed by the registering device (5) in two phases such that depending on the filling level of the breathing gas reservoir (4), the inspiration line (7) is first connected with the compressed air reserve (1) and the expiration line (8) with the breathing gas reservoir (4) during a first phase until the filling level of the breathing gas reservoir (4) reaches an upper reversing point for the valve means (6), so that the inspiration line (7) is connected with the breathing gas reservoir (4) and the expiration line (78) with the ambient air (11) during a second phase until the filling level of the breathing gas reservoir (4) reaches a lower reversing point for the valve means (6) and the latter is again reversed as in the first phase.

20 Claims, 3 Drawing Sheets

U.S. PATENT DOCUMENTS

| | | | | |
|---|---|---|---|---|
| 6,408,848 | B1 * | 6/2002 | Feldman et al. | 128/205.14 |
| 6,895,961 | B1 * | 5/2005 | Todorov | 128/201.27 |

FOREIGN PATENT DOCUMENTS

| | | |
|---|---|---|
| GB | 1 093 393 | 11/1967 |
| GB | 1 498 480 | 1/1978 |
| GB | 2 274 249 | 7/1994 |
| GB | 2 426 204 | 11/2006 |

* cited by examiner

COMPRESSED AIR RESPIRATOR

CROSS REFERENCE TO RELATED APPLICATIONS

This application claims the benefit of priority under 35 U.S.C. § 119 of German Patent Application 10 2005 023 392.9 filed May 20, 2005, the entire contents of which are incorporated herein by reference.

FIELD OF THE INVENTION

The present invention pertains to a compressed air respirator.

BACKGROUND OF THE INVENTION

The drawback of the compact compressed air respirators used hitherto as rescue or escape apparatus is the fact that not only are nearly 80 vol. % of inert gases to be carried with the compressed air reserve available for breathing, which is carried by the user of the respirator, but also that only a few vol. % of the oxygen breathed in are utilized physiologically and the rest is blown off into the environment during breathing out. On the other hand, it is advantageous in case of compressed air respirators that no special logistics and additional apparatus components are necessary, unlike in the case of recycling respirators with $CO_2$ absorbers, which are correspondingly also more expensive. It would be advantageous especially in rescue and escape apparatuses if either the operating time with a given compressed air cylinder were prolonged, i.e., if it were possible to improve the utilization of a given compressed air reserve, or if it were possible to reduce the weight of the apparatus and to make it more easily portable at a given duration of use by reducing the size of the cylinder.

Rescue and escape apparatuses are carried directly on the body and shall therefore be, in general, relatively light-weight and easily portable, so that they are therefore especially well suited for the indicated purpose.

A compressed air respirator, which is also said to be used as a rescue apparatus, is known from GB 2 274 249 A. The compressed air flows here from a compressed air cylinder via an outlet at a constant gas volume flow into a breathing gas reservoir, from which the user of the apparatus breathes in via a mouthpiece and into which he also breathes out. Breathing gas enriched with $CO_2$ is released into the environment via an expiration valve, which opens when a preset pressure is reached in the breathing gas reservoir, while compressed air flows in continuously and at a constant rate from the compressed air cylinder.

The drawback of this prior-art device is that too much fresh breathing gas is made available to the user of the apparatus when he is under low to moderate physical strain due to the compressed air flowing in at a constant rate, at any rate more than is physiologically consumed, whereas a possibly substantially larger expiration volume will enter the breathing gas reservoir with increased $CO_2$ concentration under a higher physical strain, so that the mean $CO_2$ concentration of the gas being breathed in may increase to an undesirably high value. However, a higher setting of the constant gas volume flow into the breathing gas reservoir shortens the desired longer use time of the respirator. Efficient enrichment with $CO_2$ of the expired air released into the environment from the deep regions of the lung is not achieved with the prior-art respirator.

SUMMARY OF THE INVENTION

Thus, the object of the present invention is to provide a compressed air respirator with improved utilization of the compressed air reserve in case of compressed air consumption from the compressed air reserve that is proportional to the physical strain.

According to the invention, a compressed air respirator is provided comprising a compressed air reserve with a connected demand air supply valve, a reversible breathing gas reservoir with a registering means detecting the filling level of the breathing gas reservoir, an inspiration and expiration line for the user of the apparatus and a valve or valve means connected to the inspiration and expiration line and, on an inlet side, connected with the compressed air reserve with the demand air supply valve and connected with the breathing gas reservoir and, on an outlet side, connected with ambient air and with the breathing gas reservoir. The valve is cyclically reversed by the registering means in two phases such that depending on the filling level of the breathing gas reservoir, the inspiration line is first connected with the compressed air reserve and the expiration line with the breathing gas reservoir during a first phase until the filling level of the breathing gas reservoir reaches an upper reversing point for the valve, so that the inspiration line is connected with the breathing gas reservoir and the expiration line with the ambient air during a second phase until the filling level of the breathing gas reservoir reaches a lower reversing point for the valve and the valve is again reversed as in the first phase.

An essential advantage of the compressed air respirator according to the invention is that the reversible valve means is actuated cyclically in two phases by the registering means detecting the degree of filling of the breathing gas reservoir: During a first phase, the inspiration line to the user of the apparatus is connected at first to the compressed air reserve and the expiration line from the user of the apparatus to the breathing gas reservoir until the degree of filling of the breathing gas reservoir reaches an upper reversing point for the valve means, so that the inspiration line is connected to the breathing gas reservoir and the expiration line to the ambient air during a subsequent second phase until the degree of filling of the breathing gas reservoir reaches a lower reversing point for the valve means and this will then again reverse as in the first phase, and so on. As a result, the breathing air reserve is utilized more efficiently due to controlled rebreathing from the breathing gas reservoir and the operating time is thus prolonged, and it is ensured that the amount of breathing air being consumed is proportional to the physical strain of the user of the apparatus.

An exemplary embodiment of the present invention will be explained below on the basis of the schematic figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
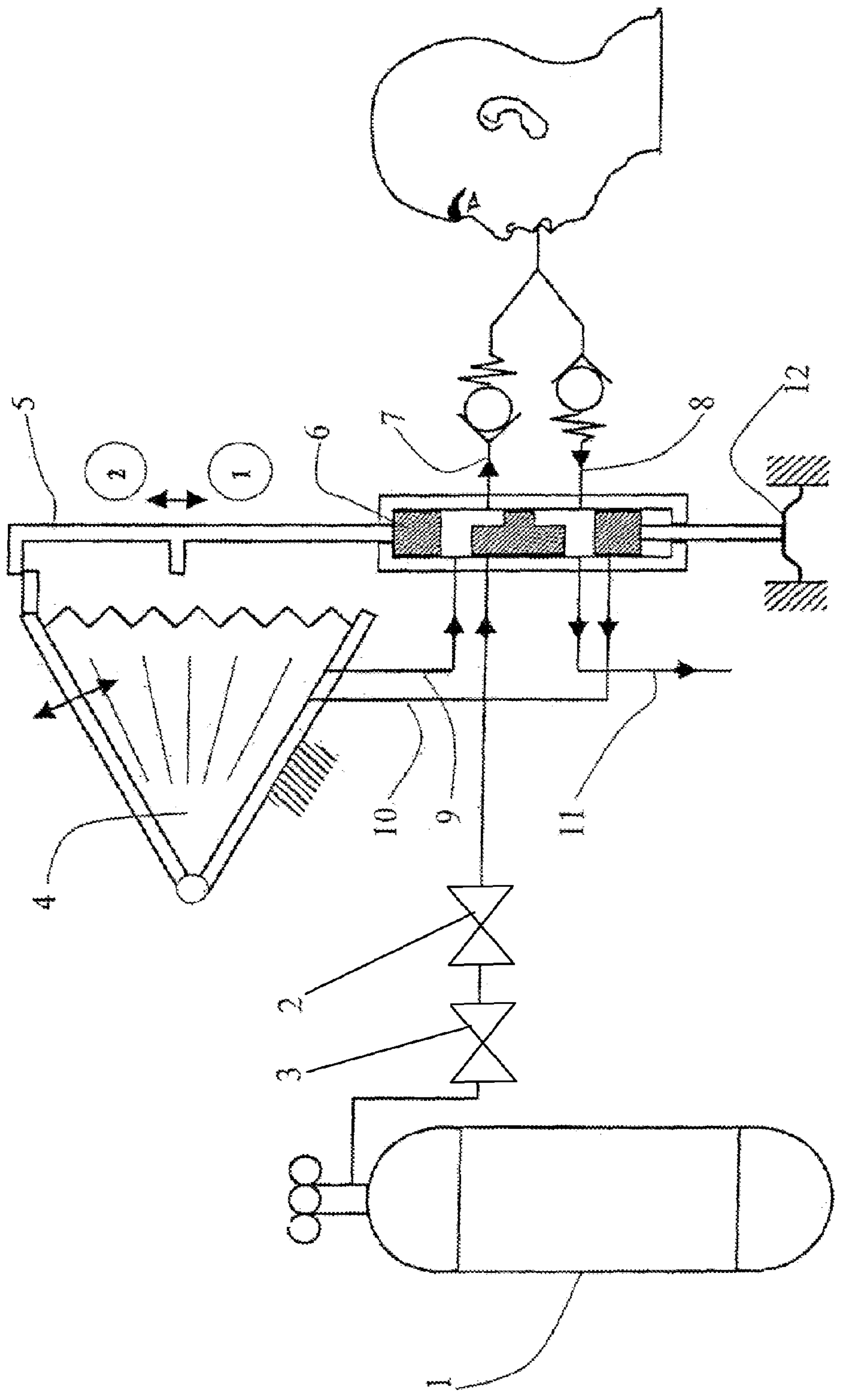
FIG. 1 is a first embodiment of a compressed air respirator with a mechanical control.

Referring to the drawings in particular, the user of the apparatus shown in FIG. 1 and in the other figures on the right-hand side first breathes in air during a first phase via the demand air supply valve 2 with a pressure reducer 3 arranged upstream via the valve means 6 preferably designed as a rotary or slide type reversing valve, corresponding to the lower valve position "1," not shown, with normal $CO_2$ concentration in the inspiration air. The demand air supply valve 2 is a breathing-controlled air dispensing means, which is known per se and is known, for example, from respirators or diving apparatuses. The demand air supply valve 2 is called "demand valve" in English. The compressed air reserve 1 is designed, in general, as a cylinder with a filling pressure of, e.g., 200 bar and an operating time of about 15 to 30 minutes during normal breathing without rebreathing. The breathing gas reservoir 4 has a reversible design and, for example, is in the form of a breathing bellows, cylinder, bag or even flexible tube. The valve means 6 is reversed during the first phase such that the expiration line 8 is connected via the admission line 10 with the breathing gas reservoir 4 and fills this over a few expirations until an upper reversing point is reached for the valve means 6, which is actuated by the registering means 5 shown as a carrier of the breathing gas reservoir 4 to move automatically into position "2" shown in FIG. 1. The user of the apparatus then breathes in in this position during the second phase of the cycle via the discharge line 9 only from the breathing gas reservoir 4, and the inspiration air from the breathing gas reservoir 4 has a mean $CO_2$ concentration of about 2.5 vol. % to 3.0 vol. %. The expiration air with a mean $CO_2$ concentration of about 5 vol. % is released during this second phase into the ambient air 11 via a line until the breathing gas reservoir 4 reaches a lower reversing point, so that the valve means 6 will again return into position "1." On the whole, the mean $CO_2$ concentration in the inspiration air is about 1.5 vol. % because equal volumes with nearly 0 vol. % of $CO_2$ are alternatingly breathed in from the compressed air reserve 1 and with a maximum of 3.0 vol. % from the breathing gas reservoir 4. The $CO_2$ concentration in the expiration air into the ambient air 11 is about 5.0 vol. % during the second phase, so that, e.g., the compressed air being carried by the user is utilized substantially better than without rebreathing.

The valve means 6, which is connected to the bistable spring membrane 12 and is preferably designed as a rotary or slide type reversing valve, is actuated during mechanical actuation by the movement of the breathing gas reservoir 4 via the registering means 5 and rotates or pushes forward or backward by one lock-in position at the end stops, so that the access to the inspiration line 7 of the user of the apparatus is connected either to the demand air supply valve 2 or to the breathing gas reservoir 4. While the user of the apparatus is breathing in fresh air from the demand air supply valve 2, the expiration air is released into the breathing gas reservoir 4 (position "1") until the breathing gas reservoir 4 is filled to the extent that the registering means 5 reversed as a carrier here will displace the registering means 6 into position "2," as a consequence of which the user of the apparatus will then breathe in from the breathing gas reservoir 4 and breathe out into the ambient air 11 until the breathing gas reservoir 4 is again emptied to the extent that the registering means 5 returns the valve means 6 into the starting position "1" and the cycle will thus start from the beginning.

Figure 2:
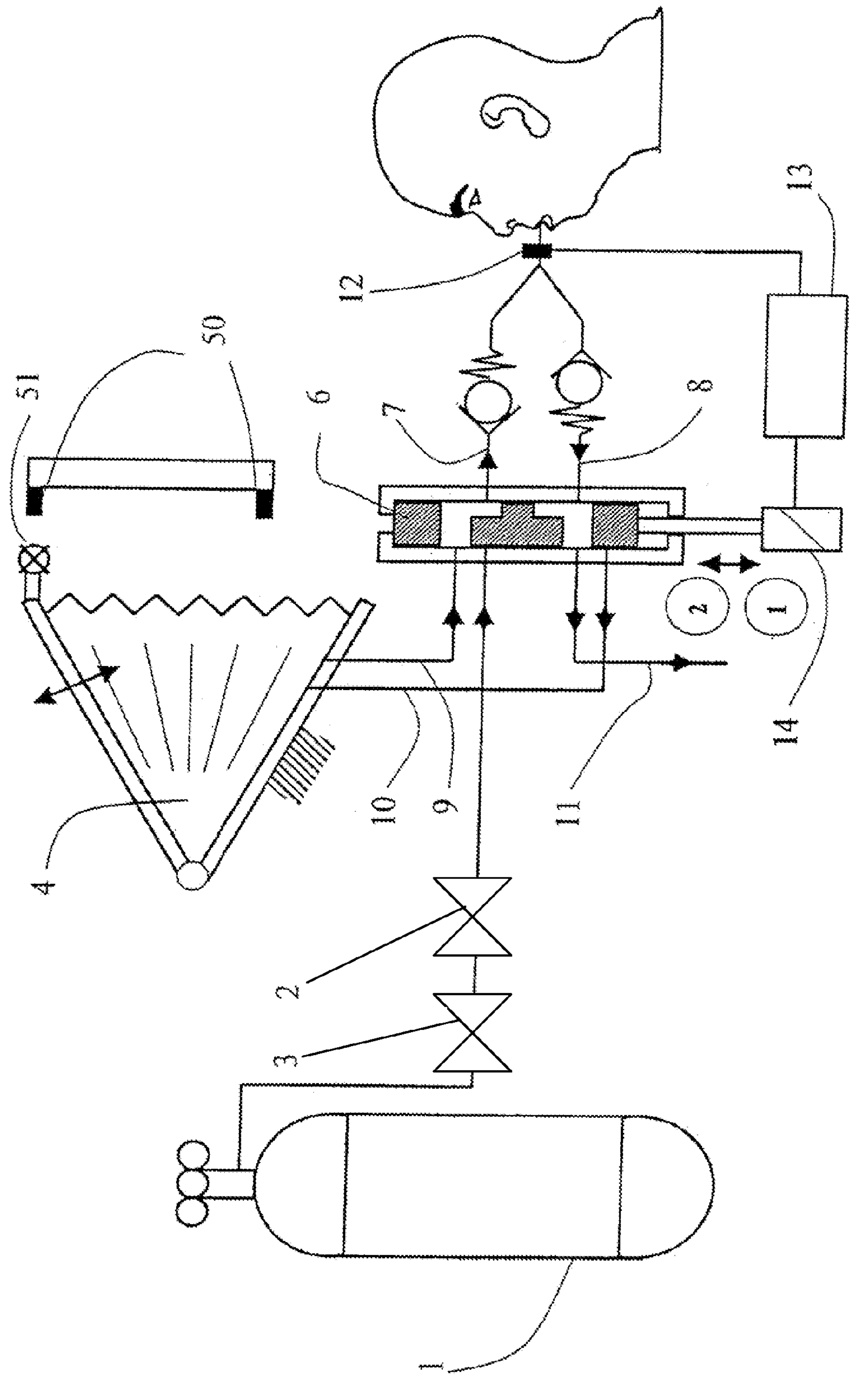
FIG. 2 is a second embodiment of a compressed air respirator with an electronic control.

A second, electronic embodiment of a compressed air respirator is shown in FIG. 2. This embodiment avoids the circumstance that a reversal is usually performed, as a rule, from position "1" to position "2" during an ongoing breath by the mechanical lever mechanism being replaced by an electro-optical means. Instead of the carrier at the breathing gas reservoir 4, an LED 51, for example, a pulsed type LED, is located here, and two photodiodes 50 are used instead of the end stops with the lever mechanism in FIG. 1. The entire device may be optically encapsulated in order to avoid interference with the function due to daylight. The function is now as follows:

The intensity of the light received is measured at the photodiodes 50. After a previous distance calibration, the distance between the LED 51 and the photodiodes 50 is measured on the basis of the intensity and the bistable valve means 6 is reversed by means of an electromagnet 14 as the end positions are being approached.

The reversal may take place during a pause between the breathing in and breathing out or between breathing out and breathing in, because it can be recognized from the change in the intensity of the measured signal at the photodiodes 50 when breathing is still taking place and when a breathing pause begins. Reversal is thus prevented from occurring during a breath. The electromagnet 14 can be alternatively actuated for reversing the valve means 6 by means of an optional gas volume flow sensor 18 and via a control means 13.

Figure 3:
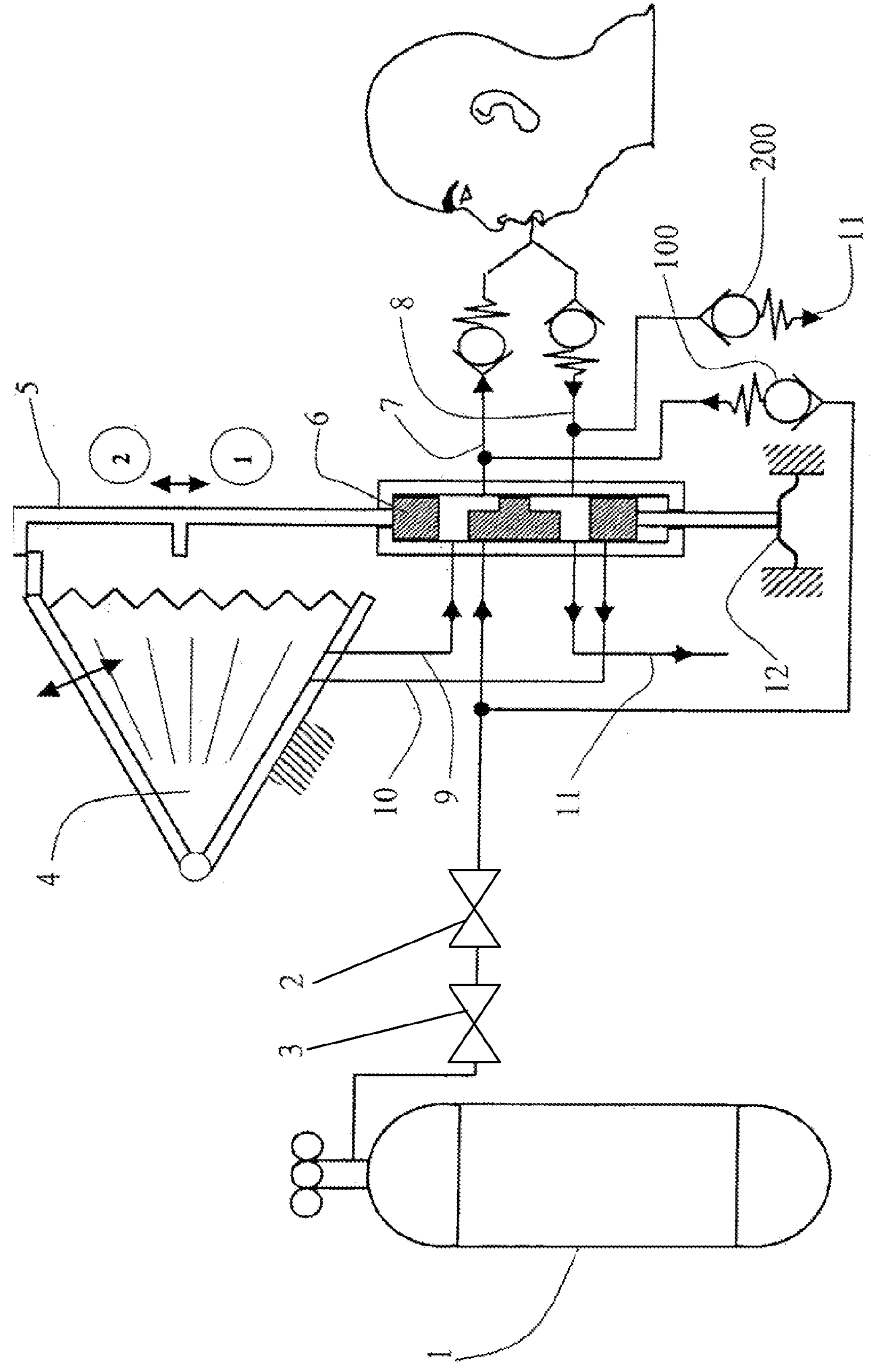
FIG. 3 is a variant of a compressed air respirator according to FIG. 1 with a bypass switch for an emergency.

FIG. 3 shows an expanded embodiment for FIG. 1, which ensures that the function of the compressed air respirator is also preserved when the valve means 6 is defective, but with the restriction that each breath is taken only once from the compressed air reserve 1 in this case. The remaining use time is reduced as a result and an increased breathing resistance is to be overcome, because the additional pressure differences of the safety valves 100, 200, which differences are increased compared to the normal operation, must be overcome, because it is ensured with the two safety valves 100, 200, which are provided for bypassing the valve means 6 and are arranged as nonreturn valves in the additional lines, that the user of the apparatus can breathe in directly from the demand air supply valve 2 and breathe out into the ambient air, i.e., that breathing can continue with the restrictions even in case of malfunction of the valve means 6.

While specific embodiments of the invention have been shown and described in detail to illustrate the application of the principles of the invention, it will be understood that the invention may be embodied otherwise without departing from such principles.

What is claimed is:

1. A compressed air respirator, comprising:

a compressed air reserve with a connected demand air supply valve;

a reversible breathing gas reservoir with a registering means detecting the filling level of said breathing gas reservoir;

an inspiration and expiration line for the user of the respirator;

an admission line;

a discharge line;

another valve connected to said inspiration and expiration line and, on an inlet side, connected with said compressed air reserve with said demand air supply valve and connected with said breathing gas reservoir via said discharge line and, on an outlet side, connected with said breathing gas reservoir via said admission line and with ambient air, said valve being cyclically reversed by said registering means in two phases such that depending on a filling level of said breathing gas reservoir, said inspiration line is first connected with said compressed air reserve and said expiration line with said breathing gas reservoir via said admission line during a first phase until the filling level of said breathing gas reservoir reaches an upper reversing point for said another valve, so that the inspiration line is connected with said breathing gas reservoir via said discharge line and said expiration line with said ambient air during a second phase until the filling level of said breathing gas reservoir reaches a lower reversing point for said another valve and said another valve is again reversed as in the first phase.

2. A compressed air respirator in accordance with claim 1, wherein said another valve is designed as a rotary or slide type valve device.

3. A compressed air respirator in accordance with claim 1, wherein said another valve is bistable.

4. A compressed air respirator in accordance with claim 1, wherein said registering means has an electro-optical design.

5. A compressed air respirator in accordance with claim 1, wherein said registering means is in mechanical or electric functional connection with said another valve.

6. A compressed air respirator in accordance with claim 1, further comprising an electromagnet, wherein said another valve is in functional connection with said electromagnet.

7. A compressed air respirator in accordance with claim 6, wherein said electromagnet is connected with a control which receives measured signals from a gas volume flow sensor as a function of an apparatus user's breathing effort for controlling said another valve.

8. A compressed air respirator in accordance with claim 1, wherein said another valve is connected to said demand air supply valve via a connection line between said demand air supply valve and said another valve and further comprising a first line containing a first safety valve and is directly connected with said connection line between said demand air supply valve and said another valve, said first line branching off from said inspiration line, and a second line, which leads to said ambient air via a second safety valve, said second line branching off from said expiration line.

9. A compressed air respirator, comprising:

a compressed air reserve with a connected demand air supply valve;

a reversible breathing gas reservoir with a registering means detecting the filling level of said breathing gas reservoir;

an inspiration line for the user of an apparatus and an expiration line for the user of the apparatus;

a valve means having an inlet side and an outlet side, said valve means being connected to said inspiration line, connected to said expiration line, connected with said compressed air reserve via said demand air supply valve on said inlet side, connected with said breathing gas reservoir via an input line on said inlet side, connected with ambient air on said outlet side, and connected with said breathing gas reservoir via said output line on said outlet side, said valve means for cyclically reversing connections depending on a filling level of said breathing gas reservoir detected by said registering means, to first connect said inspiration line with said compressed air reserve and said expiration line with said breathing gas reservoir via said output line during a first phase until the filling level of said breathing gas reservoir reaches an upper reversing point for said valve means, so that the inspiration line is connected with said breathing gas reservoir and said expiration line with said ambient air during a second phase until the filling level of said breathing gas reservoir reaches a lower reversing point for said valve means and said valve means is again reversed as in the first phase.

10. A compressed air respirator in accordance with claim 9, wherein said valve means comprises a rotary or slide type valve device.

11. A compressed air respirator in accordance with claim 9, wherein said valve means includes a bistable device for shifting between the first phase and the second phase.

12. A compressed air respirator in accordance with claim 9, wherein said registering means has an electro-optical design.

13. A compressed air respirator in accordance with claim 9, wherein said registering means is in mechanical or electric functional connection with said valve means.

14. A compressed air respirator in accordance with claim 9, further comprising an electromagnet, wherein said valve means is in functional connection with said electromagnet.

15. A compressed air respirator in accordance with claim 14, wherein said electromagnet is connected with a control which receives measured signals from a gas volume flow sensor as a function of the apparatus user's breathing effort for controlling said valve means.

16. A compressed air respirator in accordance with claim 14, wherein said valve means is connected to said demand air supply valve via a connection line between said demand air supply valve and said valve and further comprising a first line containing a first safety valve and is directly connected with said connection line between said demand air supply valve and said valve means, said first line branching off from said inspiration line, and a second line, which leads to said ambient air via a second safety valve, said second line branching off from said expiration line.

17. A compressed air respirator, comprising:

a compressed air reserve with a connected demand air supply valve;

a reversible breathing gas reservoir with a registering means detecting the filling level of said breathing gas reservoir;

an inspiration line for the user of an apparatus and an expiration line for the user of the apparatus;

a reservoir input line;

a reservoir output line;

a valve means having an inlet side and an outlet side, said valve means being connected to said inspiration line, connected to said expiration line, connected with said compressed air reserve on said inlet side via said demand air supply valve, connected with said breathing gas reservoir on said inlet side via said reservoir input line, connected with ambient air on said outlet side, and connected with said breathing gas reservoir on said outlet side via said reservoir output line, said valve means for cyclically switching between a first connection arrangement and a second connection arrangement based on a filling level of said breathing gas reservoir detected by said registering means, said valve means connecting said inspiration line with said compressed air reserve and said expiration line with said breathing gas reservoir via said reservoir output line in said first connection arrangement until the filling level of said breathing gas reservoir reaches an upper reversing point for said valve means, said breathing gas reservoir receiving expired gas via said reservoir output line in said first connection arrangement, said expired gas including carbon dioxide, said valve means connecting said inspiration line with said breathing gas reservoir and said expiration line with said ambient air in said second connection arrangement until the filling level of said breathing gas reservoir reaches a lower reversing point for said valve means and said valve means again switches to said first connection arrangement, said inspiration line receiving said expired gas from said breathing gas reservoir in said second connection arrangement.

18. A compressed air respirator in accordance with claim 17, further comprising an electromagnet, wherein said valve means is in functional connection with said electromagnet.

19. A compressed air respirator in accordance with claim 18, wherein said electromagnet is connected with a control which receives measured signals from a gas volume flow sensor as a function of the apparatus user's breathing effort for controlling said valve means.

20. A compressed air respirator in accordance with claim 18, wherein said valve means is connected to said demand air supply valve via a connection line between said demand air supply valve and said valve and further comprising a first line containing a first safety valve and is directly connected with said connection line between said demand air supply valve and said valve means, said first line branching off from said inspiration line, and a second line, which leads to said ambient air via a second safety valve, said second line branching off from said expiration line.

* * * * *